United States Patent
Horiike et al.

(10) Patent No.: US 11,129,592 B2
(45) Date of Patent: Sep. 28, 2021

(54) IMAGE DIAGNOSTIC APPARATUS AND METHOD AND PROGRAM

(71) Applicant: TERUMO KABUSHIKI KAISHA, Tokyo (JP)

(72) Inventors: Toyokazu Horiike, Fujinomiya (JP); Kenji Maeda, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 501 days.

(21) Appl. No.: 15/926,090

(22) Filed: Mar. 20, 2018

(65) Prior Publication Data

US 2018/0271477 A1     Sep. 27, 2018

(30) Foreign Application Priority Data

Mar. 21, 2017   (JP) .............................. JP2017-054838

(51) Int. Cl.
| | |
|---|---|
| *A61B 8/12* | (2006.01) |
| *A61B 5/00* | (2006.01) |
| *A61B 8/00* | (2006.01) |
| *A61B 5/02* | (2006.01) |

(Continued)

(52) U.S. Cl.
CPC .............. *A61B 8/12* (2013.01); *A61B 5/0035* (2013.01); *A61B 5/0066* (2013.01);
(Continued)

(58) Field of Classification Search
CPC ....... A61B 8/12; A61B 5/7257; A61B 8/4416; A61B 8/4438; A61B 5/02007;
(Continued)

(56) References Cited

U.S. PATENT DOCUMENTS

| | | | |
|---|---|---|---|
| 2003/0195419 A1* | 10/2003 | Harada | A61B 8/481 |
| | | | 600/437 |
| 2012/0172698 A1 | 7/2012 | Teo et al. | |
| 2016/0206290 A1* | 7/2016 | Itoh | A61B 8/5261 |

FOREIGN PATENT DOCUMENTS

| | | |
|---|---|---|
| EP | 2 484 288 A1 | 8/2012 |
| JP | H11-056752 A | 3/1999 |

(Continued)

OTHER PUBLICATIONS

The extended European Search Report dated Jun. 19, 2018, by the European Patent Office in corresponding European Patent Application No. 18162750.6-1124. (8 pages).

(Continued)

*Primary Examiner* — Pascal M Bui Pho
*Assistant Examiner* — Adil Partap S Virk
(74) *Attorney, Agent, or Firm* — Buchanan Ingersoll & Rooney PC

(57) ABSTRACT

An imaging apparatus for diagnosis is disclosed, which has a motor drive unit (MDU) configured to be connected to a catheter, and which generates a vascular optical coherence tomographic image and an ultrasound tomographic image of a subject, based on a signal output from the catheter. The apparatus includes a first inspection unit that inspects the presence or absence of the ultrasound transceiver, based on intensity distribution of the electric signal of the reflected wave which is obtained by a first drive unit, and a second inspection unit that generates line image data in a radial direction, regarding a position of the imaging core as an origin, based on the electric signal of the interference light which is obtained by a second drive unit, and that inspects the presence or absence of the optical transceiver, based on pixel data distribution within a predetermined range from a position of the origin.

20 Claims, 9 Drawing Sheets

(51) Int. Cl.
*A61B 8/15* (2006.01)
*A61B 8/08* (2006.01)

(52) U.S. Cl.
CPC .......... *A61B 5/0073* (2013.01); *A61B 5/0084* (2013.01); *A61B 5/02007* (2013.01); *A61B 5/7445* (2013.01); *A61B 8/15* (2013.01); *A61B 8/4416* (2013.01); *A61B 8/4438* (2013.01); *A61B 8/58* (2013.01); *A61B 5/004* (2013.01); *A61B 5/6852* (2013.01); *A61B 5/7257* (2013.01); *A61B 8/4461* (2013.01); *A61B 8/5261* (2013.01)

(58) Field of Classification Search
CPC ... A61B 5/0073; A61B 5/0084; A61B 5/0035; A61B 8/58; A61B 5/7445; A61B 8/15; A61B 5/0066; A61B 5/6852; A61B 8/5261; A61B 5/004; A61B 8/4461
See application file for complete search history.

(56) References Cited

FOREIGN PATENT DOCUMENTS

| | | |
|---|---|---|
| JP | 2000-152940 A | 6/2000 |
| JP | 2006-204430 A | 8/2006 |
| JP | 2015-070939 A | 4/2015 |
| WO | 2015/045353 A1 | 4/2015 |
| WO | 2016/083379 A1 | 6/2016 |
| WO | WO-2016083379 A1 * | 6/2016 ............... A61B 8/12 |

OTHER PUBLICATIONS

Notice of Reasons for Refusal issued by the Japanese Patent Office in corresponding Japanese Patent Application No. 2017-054838 dated Aug. 18, 2020 (4 pages including partial English translation).

* cited by examiner

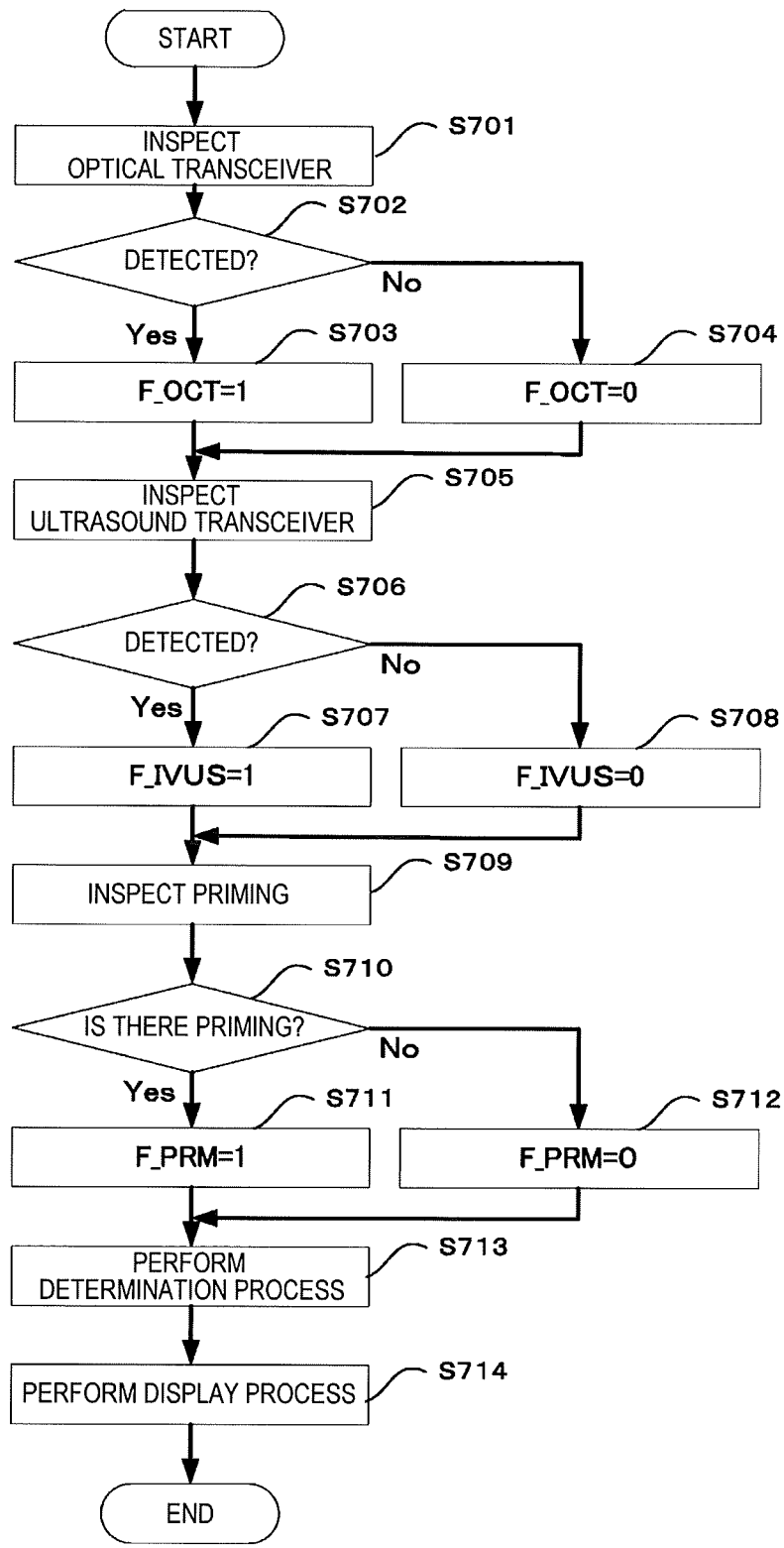

IMAGE DIAGNOSTIC APPARATUS AND METHOD AND PROGRAM

CROSS-REFERENCES TO RELATED APPLICATIONS

This application claims priority to Japanese Application No. 2017-054838 filed on Mar. 21, 2017, the entire content of which is incorporated herein by reference.

TECHNICAL FIELD

The present disclosure relates to an imaging apparatus for diagnosis using a catheter, and an operation method and a program thereof.

BACKGROUND ART

As an apparatus for diagnosing a vascular lumen, an intravascular ultra sound (IVUS) apparatus, and optical coherence tomography (OCT) apparatus are known. In addition, the OCT has been further developed, and optical frequency domain imaging (OFDI) utilizing wavelength sweep is known.

An ultrasound wave has a property in which the ultrasound wave reaches a relatively deep site of a vascular tissue. Accordingly, a vascular tomographic image obtained using the IVUS can be suitably used in order to diagnose not only a surface of the vascular tissue but also the deep site. On the other hand, light used for the OCT or the OFDI does not reach a deep tissue compared to the ultrasound wave. However, an intravascular wall image having extremely high resolution can be obtained compared to that of the IVUS.

The configuration is adopted as described above. Accordingly, the following imaging apparatus for diagnosis has recently been proposed. A catheter, which accommodates both an ultrasound transceiver and an optical transceiver, that is, a hybrid type catheter, is used so as to generate both images of an ultrasound tomographic image and an optical tomographic image (JP-A-11-56752 and JP-A-2006-204430).

In a case of using this type apparatus, the catheter is connected to a motor drive unit (MDU) for rotating and moving an internally provided imaging core.

In a case of an imaging apparatus for diagnosis which can generate both images of an ultrasound tomographic image and an optical tomographic image, catheters which can be connected to an MDU thereof include not only the hybrid catheter but also a catheter dedicated to IVUS and a catheter dedicated to OCT. Therefore, there is a possibility that the type of the catheter actually connected to the MDU may not be the type intended by a user (physician).

In the imaging apparatus for diagnosis, the optical tomographic image and the ultrasound tomographic image are displayed on a display device, based on a signal output from the catheter connected to the MDU. Therefore, the user (physician) can presume the type of the connected catheter, based on the optical tomographic image and the ultrasound tomographic image, which are displayed. For example, in a case where the optical tomographic image is an abnormal image and the ultrasound tomographic image is a familiar image, the user can presume that the connected catheter is the catheter dedicated to IVUS. However, this shows a case where the user has experience of a medical procedure using a plurality of types of catheters. An inexperienced user is less likely to presume the catheter. Even a user having sufficient experience wants information, which leads to confirmation of his/her, own presumption.

SUMMARY OF THE INVENTION

In accordance with an exemplary embodiment, a technique is disclosed for determining a type of catheter connected to an MDU without adding any special hardware.

In order to solve the above-described problem, for example, the imaging apparatus for diagnosis according to the present disclosure has the following configurations. That is, an imaging apparatus for diagnosis is disclosed, which has a motor drive unit (MDU) for being connected to a catheter and for moving and rotating an imaging core accommodated in the catheter along a longitudinal direction of the catheter, and which generates a vascular optical coherence tomographic image and an ultrasound tomographic image of a subject, based on a signal output from the catheter. The apparatus includes a first drive unit that applies an ultrasound drive signal to an ultrasound transceiver accommodated in a distal portion of an imaging core, and acquires an electric signal indicating a reflected wave, assuming that the catheter is connected to the MDU, a first inspection unit that inspects the presence or absence of the ultrasound transceiver, based on intensity distribution of the electric signal of the reflected wave which is obtained by the first drive unit, a second drive unit that supplies light to an optical transceiver accommodated in the distal portion of the imaging core, and acquires an electric signal indicating interference light, assuming that the catheter is connected to the MDU, a second inspection unit that generates line image data in a radial direction, regarding a position of the imaging core as an origin, based on the electric signal of the interference light which is obtained by the second drive unit, and that inspects the presence or absence of the optical transceiver, based on pixel data distribution within a predetermined range from a position of the origin, and a determination unit that determines whether the catheter connected to the MDU is any one of the catheter dedicated to diagnosis of the ultrasound tomographic image, the catheter dedicated to diagnosis of the optical coherence tomographic image, and the catheter corresponding to both the ultrasound tomographic image and the optical coherence tomographic image, based on an inspection result of the first inspection unit and an inspection result of the second inspection unit.

An operation method of an imaging apparatus for diagnosis which has a motor drive unit (MDU) configured to be connected to a catheter and for moving and rotating an imaging core accommodated in the catheter along a longitudinal direction of the catheter, and which generates a vascular optical coherence tomographic image and an ultrasound tomographic image of a subject, based on a signal output from the catheter, the method comprising: a first drive process in which a first drive unit applies an ultrasound drive signal to an ultrasound transceiver accommodated in a distal portion of an imaging core, and acquires an electric signal indicating a reflected wave, assuming that the catheter is connected to the MDU; a first inspection process in which a first inspection unit inspects a presence or an absence of the ultrasound transceiver, based on intensity distribution of the electric signal of the reflected wave which is obtained by the first drive process; a second drive process in which a second drive unit supplies light to an optical transceiver accommodated in the distal portion of the imaging core, and acquires an electric signal indicating interference light, assuming that the catheter is connected to the MDU; a second inspection process in which a second inspection unit generates line image data in a radial direction, regarding a position of the imaging core as an origin, based on the electric signal of the interference light which is obtained by the second drive process, and inspects a presence or an absence of the optical transceiver, based on pixel data distribution within a predetermined range from a position of the origin; and a determination process in which a determination unit determines whether the catheter connected to the MDU is any one of the catheter dedicated to diagnosis of the ultrasound tomographic image, the catheter dedicated to diagnosis of the optical coherence tomographic image, and the catheter corresponding to both the ultrasound tomographic image and the optical coherence tomographic image, based on an inspection result of the first inspection unit and an inspection result of the second inspection unit.

A method is disclosed for determining a type of catheter connected to a motor drive unit (MDU) of an imaging apparatus for diagnosis, wherein the MDU is configured to be connected to a catheter and to move and rotate an imaging core accommodated in the catheter along a longitudinal direction of the catheter, and configured to generate a vascular optical coherence tomographic image and an ultrasound tomographic image of a subject, based on a signal output from the catheter, the method comprising: applying an ultrasound drive signal to an ultrasound transceiver accommodated in a distal portion of an imaging core, and acquiring an electric signal indicating a reflected wave, assuming that the catheter is connected to the MDU; determining a presence or an absence of the ultrasound transceiver, based on intensity distribution of the electric signal of the reflected wave which is acquired; supplying light to an optical transceiver accommodated in the distal portion of the imaging core, and acquiring an electric signal indicating interference light, assuming that the catheter is connected to the MDU; generating line image data in a radial direction, regarding a position of the imaging core as an origin, based on the electric signal of the interference light which is acquired, and inspecting a presence or an absence of the optical transceiver, based on a pixel data distribution within a predetermined range from a position of the origin; and determining whether the catheter connected to the MDU is any one of the catheter dedicated to diagnosis of the ultrasound tomographic image, the catheter dedicated to diagnosis of the optical coherence tomographic image, and the catheter corresponding to both the ultrasound tomographic image and the optical coherence tomographic image, based on the intensity distribution of the electric signal of the reflected wave and/or the pixel data distribution within the predetermined range from the position of the origin.

According to the present disclosure, a type of catheters connected to an MDU can be determined without adding any special hardware.

BRIEF DESCRIPTION OF THE DRAWINGS

FIG. 7 is a flowchart illustrating a process of determining a type of catheters according to the exemplary embodiment.

DETAILED DESCRIPTION

Hereinafter, each embodiment according to the present disclosure will be described in detail with reference to the accompanying drawings.

Figure 1:
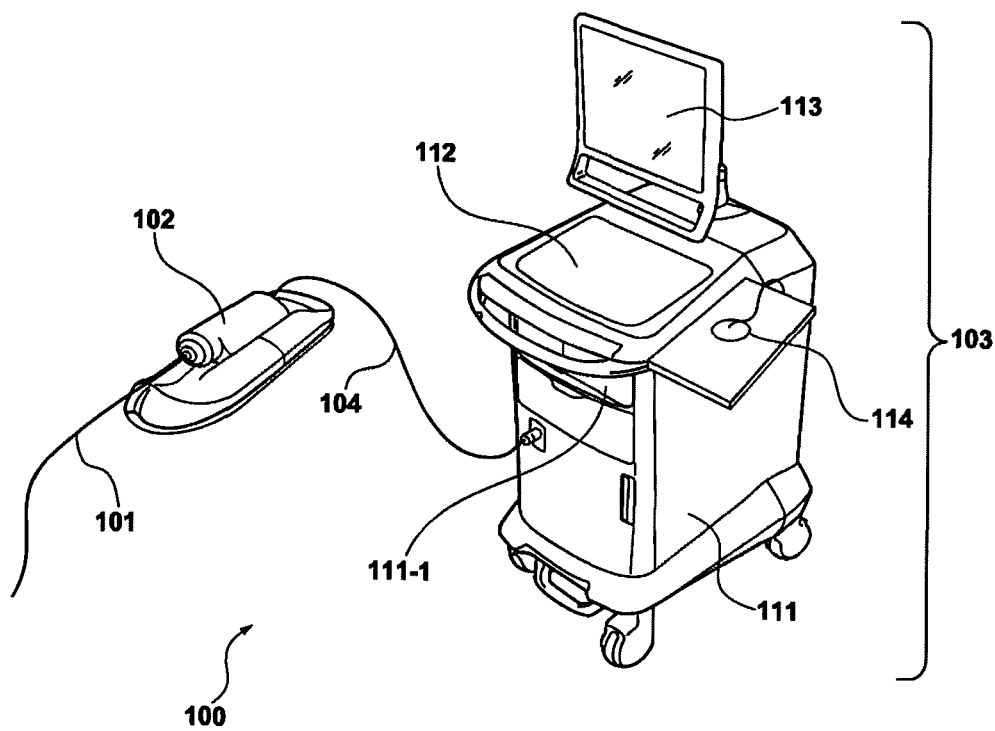
FIG. 1 is a view illustrating an external configuration of an imaging apparatus for diagnosis according to an exemplary embodiment.

FIG. 1 is a view illustrating an external configuration of an imaging apparatus for diagnosis 100 according to the embodiment.

As illustrated in FIG. 1, the imaging apparatus for diagnosis 100 includes a catheter 101, a motor drive unit (hereinafter, referred to as an MDU) 102, and an operation control device 103. The MDU 102 and the operation control device 103 are connected to each other via a cable 104 accommodating a signal line and an optical fiber.

In the operation control device 103, the reference numeral 111 represents a main body control unit. The main body control unit 111 generates line data extending from a rotation center position in a radial direction, based on a signal (an ultrasound wave emitted toward a vascular tissue and a reflected wave of light) obtained by an imaging core accommodated inside the catheter 101. Then, through an interpolation process of the line data, a vascular tomographic image having each property can be generated based on the ultrasound wave and optical interference.

The reference numeral 111-1 represents a printer & DVD recorder, which prints a processing result in the main body control unit 111 or stores the processing result as data. A storage destination of the processing result may be a server or a USB memory, and a type of the storage destination is not limited. The reference numeral 112 represents an operation panel. A user inputs various setting values and instructions via the operation panel 112. The reference numeral 113 represents a monitor (LCD) serving as a display, which displays various tomographic images generated in the main body control unit 111. The reference numeral 114 represents a mouse serving as a pointing device (coordinate input device).

The catheter 101 is directly inserted into a blood vessel. Then, the catheter 101 is movable in the longitudinal direction, and has a structure for accommodating a rotatable imaging core. In a case of a hybrid catheter, a distal housing of the imaging core is provided with an ultrasound transceiver which generates an ultrasound wave, based on a signal transmitted from the imaging apparatus for diagnosis 100 and which receives and converts the ultrasound wave reflected from a vascular tissue into an electric signal, and an optical transceiver which continuously transmits transmitted light (measurement light) into the blood vessel and which continuously receives the light reflected from the inside of the blood vessel. Then, a drive shaft for transmitting rotation force and moving force of the imaging core from the MDU 102 is connected to the housing. That is, the imaging core is configured to include the housing and the drive shaft. In the imaging apparatus for diagnosis 100, the catheter 101, which accommodates the imaging core, is used so as to measure an internal state of the blood vessel.

The MDU 102 has a portion engaging with a connection portion in a proximal end of the catheter 101. In a case where the catheter 101 is a hybrid type catheter, the MDU 102 functions as a relay device between the ultrasound transceiver and the optical transceiver in the imaging core inside the catheter 101, and the operation control device 103. In addition, the MDU 102 drives a built-in motor. In this manner, the MDU 102 performs a process of pulling a hand-side inner tube and the drive shaft from a hand-side outer tube of the catheter 101, and controls the rotation of the drive shaft.

In addition, various switches and buttons are disposed in the MDU 102, and a user (physician) operates the switches and buttons, thereby enabling the imaging core inside the catheter 101 to be rotationally driven and pulled back (movement of the imaging core).

Figure 2:
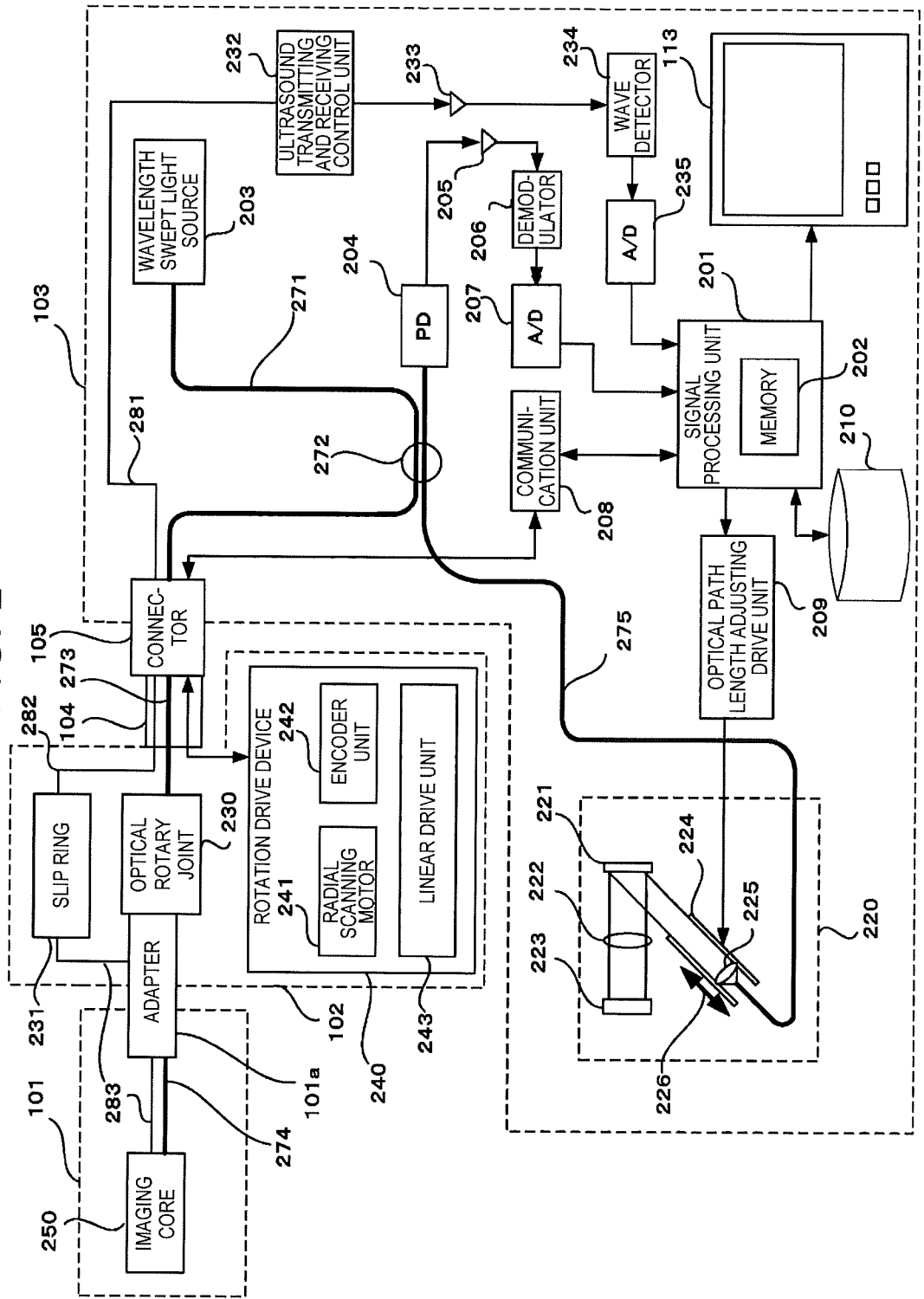
FIG. 2 is a block configuration diagram of the imaging apparatus for diagnosis.

FIG. 2 illustrates a block configuration diagram of the imaging apparatus for diagnosis 100 according to the embodiment. Hereinafter, referring to FIG. 2, a configuration of the imaging apparatus for diagnosis according to the embodiment will be described.

In the illustration, the reference numeral 201 represents a signal processing unit which controls the overall imaging apparatus for diagnosis, and the signal processing unit is configured to include several circuits including a microprocessor. The reference numeral 210 is a non-volatile storage device represented by a hard disk, and stores various programs or data files executed by the signal processing unit 201. The reference numeral 202 represents a memory (RAM) installed inside the signal processing unit 201. The reference numeral 203 represents a wavelength swept light source, and is a light source, which repeatedly generates light having a wavelength that varies within a preset range along a time axis.

The light output from the wavelength swept light source 203 is incident on one end of a first single mode fiber 271, and is transmitted toward the distal side. The first single mode fiber 271 is optically coupled to a fourth single mode fiber 275 in an intermediately provided optical fiber coupler 272.

The light incident on the first single mode fiber 271 and emitted from the optical fiber coupler 272 to the distal side can be guided to a second single mode fiber 273 via a connector 105. The other end of the second single mode fiber 273 is connected to an optical rotary joint 230 inside the MDU 102.

In accordance with an exemplary embodiment, the catheter 101 has an adapter 101a for being connected to the MDU 102. Then, the catheter 101 is connected to the MDU 102 by using the adapter 101a, thereby allowing the catheter 101 to be stably held in the MDU 102. Furthermore, an end portion of a third single mode fiber 274 rotatably accommodated inside the catheter 101 is connected to the optical rotary joint 230. As a result, the second single mode fiber 273 and the third single mode fiber 274 can be optically coupled to each other. The other end (leading portion side of the catheter 101) of the third single mode fiber 274 is provided with an imaging core 250 having an optical transceiver (details to be described with reference to FIG. 3) configured to include a mirror and a lens for emitting the light in a direction substantially orthogonal to the rotation axis.

As a result, the light emitted by the wavelength swept light source 203 is guided to the imaging core 250 disposed in an end portion of the third single mode fiber 274 via the first single mode fiber 271, the second single mode fiber 273, and the third single mode fiber 274. The optical transceiver of the imaging core 250 emits the light in a direction orthogonal to the axis of the fiber, and receives that reflected light. The received reflected light is conversely guided this time, and is returned to the operation control device 103.

In accordance with an exemplary embodiment, an optical path length adjusting mechanism 220 for finely adjusting an optical path length of reference light is disposed in an opposite end portion of the fourth single mode fiber 275 coupled to the optical fiber coupler 272. The optical path length adjusting mechanism 220 functions as an optical path length changing unit that changes the optical path length corresponding to fluctuations in the length so that the fluctuations in the length of the individual catheter 101 can be absorbed in a case where the catheter 101 is replaced. Therefore, a collimating lens 225 located in the end portion of the fourth single mode fiber 275 is disposed on a one-axis stage 224 which is movable as indicated by an arrow 226 showing the optical axis direction.

Specifically, in a case where the catheter 101 is replaced, the one-axis stage 224 functions as the optical path length changing unit having a variable range of the optical path length which can absorb the fluctuations in the optical path length of the catheter 101. Furthermore, the one-axis stage 224 also has a function as an adjusting unit that adjusts an offset. For example, even in a case where the distal end of the catheter 101 is not in close contact with a surface of a biological tissue, the optical path length can be finely changed by using the one-axis stage. In this manner, a state in which the reference light is interfered with the reflected light from a position of the surface of the biological tissues can be set.

The optical path length is finely adjusted by using the one-axis stage 224, and the light reflected on a mirror 223 via a grating 221 and a lens 222 is guided again to the fourth single mode fiber 275. In the optical fiber coupler 272, the light is mixed with the light obtained from the second single mode fiber 273 side, and is received by a photodiode 204 as interference light.

The interference light received by the photodiode 204 in this way is photo-electrically converted, and can be amplified by an amplifier 205. Thereafter, the interference light can be input to a demodulator 206. In the demodulator 206, demodulation processing for extracting only a signal portion of the interference light is performed, and the output is input to an A/D converter 207 as an interference light signal.

In the A/D converter 207, 2,048 points of the interference light signal can be sampled at 90 MHz, for example, thereby generating 1 line of digital data (interference light data). In accordance with an exemplary embodiment, the reason that a sampling frequency is set to 90 MHz can be based on the assumption that in a case where a repetition frequency of the wavelength sweeping is set to 40 kHz, approximately 90% of a wavelength sweeping cycle (25 μsec) is extracted as the digital data of 2,048 points. A configuration is not particularly limited thereto.

In accordance with an exemplary embodiment, the interference light data in line units generated by the A/D converter 207 is input to the signal processing unit 201, and is temporarily stored in a memory 202. Then, in the signal processing unit 201, the interference light data is subjected to frequency decomposition by using the fast Fourier transform (FFT), thereby generating data in a depth direction (line data). Based on the line data, the signal processing unit 201 constructs an optical tomographic image at each position inside the blood vessel. In some cases, the signal processing unit 201 outputs the optical tomographic image to an LCD monitor 113 at a predetermined frame rate.

The signal processing unit 201 can be further connected to an optical path length adjusting drive unit 209 and a communication unit 208. The signal processing unit 201 controls (controls the optical path length) a position of the one-axis stage 224 via the optical path length adjusting drive unit 209.

The communication unit 208 is internally equipped with several driving circuits, and communicates with the MDU 102 under the control of the signal processing unit 201. Specifically, a drive signal is supplied to a radial scanning motor for causing the optical rotary joint inside the MDU 102 to rotate the third single mode fiber, a signal is received from an encoder unit 242 for detecting the rotational position of the radial scanning motor, and a drive signal is supplied to a linear drive unit 243 for pulling the third single mode fiber 274 at predetermined speed.

The above-described process in the signal processing unit 201 is realized by causing a computer to execute a predetermined program.

In the above-described configuration, if the catheter 101 is located at a diagnosis target blood vessel position (such as a coronary artery) of a patient, a guiding catheter is pulled toward the distal end of the catheter 101 by a user's operation, and a light-transmitting flush liquid is discharged into the blood vessel through the guiding catheter. The reason is to exclude the influence of blood. Then, if the user inputs an instruction to start scanning, the signal processing unit 201 drives the wavelength swept light source 203 so as to drive the radial scanning motor 241 and the linear drive unit 243 (hereinafter, a light emitting and light receiving process performed by driving the radial scanning motor 241 and the linear drive unit 243 is referred to as scanning). As a result, the wavelength swept light can be supplied from the wavelength swept light source 203 to the imaging core 250 through the above-described path. In this case, the imaging core 250 located at the distal position of the catheter 101 rotates and moves along the rotation axis. Accordingly, while the imaging core 250 rotates and moves along the blood vessel axis, the imaging core 250 emits the light to a surface of the vascular lumen, and receives the reflected light.

Figure 4:
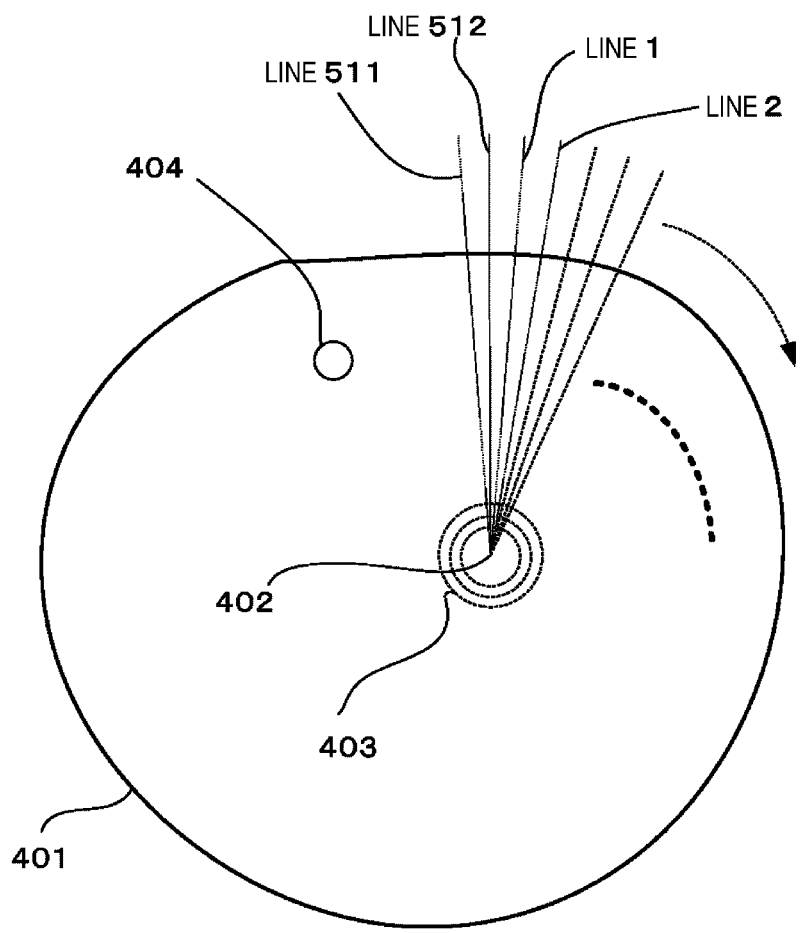
FIG. 4 is a view for describing a principle of generating a vascular tomographic image according to the exemplary embodiment.

Here, a process for generating one optical tomographic image will be briefly described with reference to FIG. 4. FIG. 4 is a view for describing a process of reconstructing a tomographic image of a luminal surface 401 of the blood vessel where the imaging core 250 is located. While the imaging core 250 is rotated once ($2\pi=360$ degrees), measurement light is transmitted and received multiple times. The light is transmitted and received once, thereby enabling the imaging core 250 to obtain data of one line in the light emitting direction. The data is subjected to the fast Fourier transform (FFT), thereby obtaining line data showing light reflection intensity (or absorption) at each position in the radial direction from the rotation center position. Therefore, while the imaging core 250 is rotated once, the light is transmitted and received 512 times, for example. In this manner, the line data of 512 lines extending radially from a rotation center 402 can be obtained. The 512 lines of the line data are close to each other in the vicinity of the rotation center position, and are farther from each other as the lines are separated from the rotation center position. Therefore, pixels in a vacant space of each line are generated after being subjected to known interpolation processing, thereby generating a two-dimensional tomographic image which is visible to a human being. Then, the generated two-dimensional tomographic images are connected to each other along the blood vessel axis. In this manner, a three-dimensional blood vessel image can be obtained. The center position of the two-dimensional tomographic image coincides with the rotation center position of the imaging core 250. However, it should be noted that the center position of the two-dimensional tomographic image is not the center position of the vascular tomographic image. In addition, although the light is weak, the light is reflected on the lens surface of the imaging core 250 and the surface of the catheter sheath. Accordingly, some concentric circles are generated with respect to the rotation central axis, as indicated by the illustrated reference numeral 403. In addition, the illustrated reference numeral 404 represents an image indicating that the guide wire is present at that position. When the optical tomographic image is constructed, the guide wire has extremely strong intensity of the reflected light, compared to the vascular tissue. Accordingly, it is possible to relatively easily find the line data in which the guide wire is present.

Next, a configuration and process content of image formation using the ultrasound wave will be described.

Scanning using the ultrasound wave is performed simultaneously with the scanning using the above-described optical interference. That is, the scanning is performed while the imaging core 250 is rotated and moved inside a catheter sheath of a probe 101. During this period, the ultrasound transceiver accommodated in the imaging core 250 emits the ultrasound wave, and detects the reflected wave. Therefore, it is necessary to generate a drive electric signal for driving the ultrasound transceiver accommodated in the imaging core 250, and to receive a reflected signal of the ultrasound wave output by the ultrasound transceiver. An ultrasound transmitting/receiving control unit 232 transmits the drive signal, and receives the reflected signal. The ultrasound transmitting/receiving control unit 232 and the imaging core 250 are connected to each other via signal line cables 281, 282, and 283. Since the imaging core 250 is rotated, the signal line cables 282 and 283 are electrically connected to each other via a slip ring 231 disposed inside the MDU 102. In the illustration, the signal line cables 281 to 283 are illustrated so that all of these are connected by a single line. However, actually, all of these are accommodated using a plurality of signal lines.

In accordance with an exemplary embodiment, the ultrasound transmitting/receiving control unit 232 is operated under the control of the signal processing unit 201, and drives the ultrasound transceiver accommodated in the imaging core 250, thereby generating an ultrasound pulse waves. The ultrasound transceiver converts the reflected wave from the vascular tissue into an electric signal, and supplies the electric signal to the ultrasound transmitting/receiving control unit 232. The ultrasound transmitting/receiving control unit 232 outputs the received ultrasound signal to an amplifier 233 so as to amplify the ultrasound signal. Thereafter, the amplified ultrasound signal is supplied to the signal processing unit 201 as ultrasound data via a wave detector 234 and an A/D converter 235, and is temporarily stored in the memory 202. In accordance with an exemplary embodiment, the A/D converter 235 samples 2,000 points of the ultrasound signal output from the wave detector 234 at 306 MHz, thereby generating digital data (ultrasound data) of one line. For example, here, 306 MHz can be set. However, this frequency is calculated on the assumption that 2,000 points are sampled for a depth of 5 mm when the sound speed is set to 1,530 m/sec. Therefore, the sampling frequency is not particularly limited thereto.

The signal processing unit 201 generates the line data corresponding to a gray scale, based on the ultrasound data stored in the memory 202. Subsequent to this process, similarly to the process of reconstructing the optical tomographic image, the lines of each line data are two-dimensionally and radially arrayed, and are subjected to interpolation processing, thereby generating the ultrasound tomographic image at each position inside the blood vessel.

Figure 8:
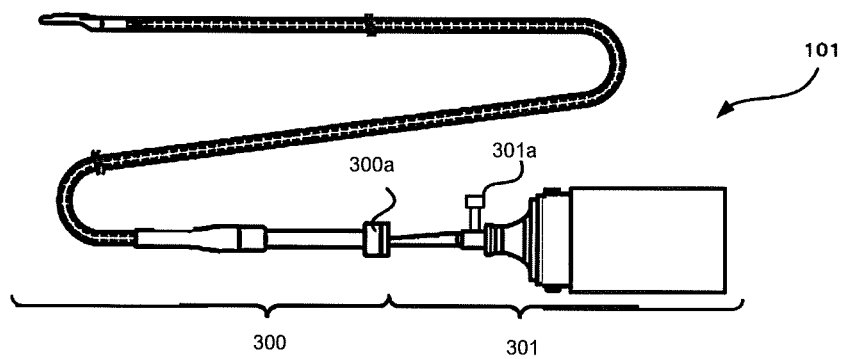
FIG. 8 is a view illustrating an external structure of the catheter according to the exemplary embodiment.

FIG. 8 illustrates an external configuration diagram of the catheter 101. The catheter 101 is configured to include an outer tube sheath 300 and an inner tube 301 accommodated inside the outer tube sheath 300 and inserted so as to be freely movable in the delivery direction. In addition, a latch section 300a is disposed in or near the rear end of the outer tube sheath 300, and the latch section 300a can be fixedly supported by the MDU 102. In addition, in a state where the rear end portion of the inner tube 301 is gripped, the MDU 102 performs an operation of pulling the inner tube 301 in the illustrated rightward direction, and an operation of rotating the drive shaft interlocked inside the inner tube 301. In FIG. 8, the reference numeral 301a represents a priming port (inlet port of a liquid (generally, a saline solution) for discharging air inside the outer tube sheath 300 and the inner tube 301).

Figure 3:
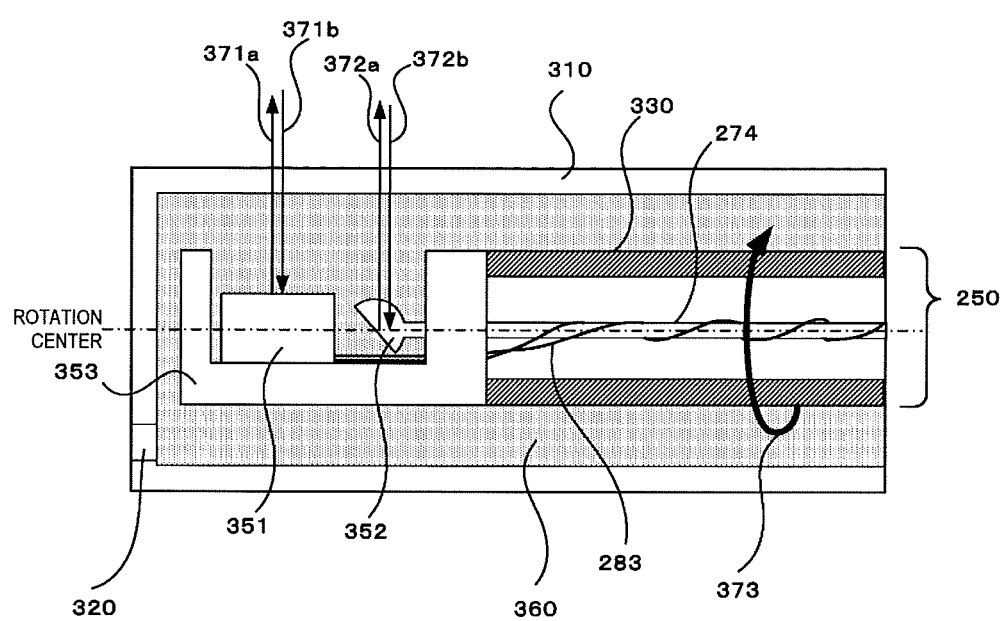
FIG. 3 is a cross-sectional view of a structure of a distal portion of the catheter according to the exemplary embodiment.

FIG. 3 illustrates a cross-sectional structure of a distal portion (side inserted into the blood vessel) in a case where the catheter 101 is the hybrid type according to an exemplary embodiment.

The inner tube 301 is inserted into the outer tube sheath 300. In a sheath 310 in the outer tube sheath 300, at least a distal portion of the sheath 310 can be configured to include a transparent material for maintaining light permeability. In addition, the distal end of the sheath 310 is provided with a priming hole 320 for discharging air bubbles inside the outer tube sheath 300 and the inner tube 301 and filling the inside of the sheath 310 with the priming solution. In a case of the OCT, even if an optical path medium is air, the optical coherence tomographic image is less affected when the optical coherence tomographic image is constructed. However, if the air is present on a propagation path of the ultrasound wave, there can be a big acoustic impedance difference between the air and a material of the catheter sheath or the blood. Accordingly, before the ultrasound wave reaches a biological tissue, the ultrasound wave is reflected on the sheath or the blood interface. Consequently, sufficient energy for capturing the image does not permeate the biological tissue. Therefore, the ultrasound wave can be diffused, and attenuates greatly. The illustrated reference numeral 360 in FIG. 2 represents the priming solution injected from the priming port 301a in FIG. 8.

In addition, an imaging core 250 which is rotatable along an arrow 373 illustrated in the drawing can be accommodated inside the sheath 310. In accordance with an exemplary embodiment, the distal end of the imaging core 250 can be provided with an ultrasound transceiver 351, an optical transceiver 352, and a housing 353 for accommodating both of these. In addition, the housing 353 is supported by the drive shaft 330. In accordance with an exemplary embodiment, the drive shaft 330 is made of a flexible material, and has such a characteristic that the rotation can be satisfactorily transmitted from the MDU 102. For example, the drive shaft 330 can be configured to include multiplex/multilayer close contact coils made of a metal wire such as stainless steel. The drive shaft 330 has substantially the same length as that of the inner tube 301. In addition, a signal line cable 283 electrically connected to the ultrasound transceiver 351 and a third single mode fiber 274 optically connected to the optical transceiver 352 are accommodated in the longitudinal direction inside the drive shaft 330.

The ultrasound transceiver 351 is provided so that the imaging core 250 according to the embodiment functions as the IVUS, and transmits the ultrasound wave toward an arrow 371a in accordance with a signal applied from the signal line cable 283. In a case where a reflected wave 371b is received from the vascular tissue, the ultrasound transceiver 351 transmits the received ultrasound wave to the MDU 102 (finally, to the operation control device 103) via the signal line cable 283, as an electric signal. When the ultrasound transceiver 351 is inserted into and scans the blood vessel, the drive shaft 330 and the imaging core 250 are rotated along the arrow 373. Accordingly, the ultrasound transceiver 351 repeatedly transmits and receives the ultrasound wave within a plane orthogonal to the rotation axis. As a result, the tomographic image orthogonal to the blood vessel axis can be obtained.

In addition, the optical transceiver 352 is provided so that the imaging core 250 according to the embodiment functions as the OCT (or the OFDI), and is configured to include a mirror having an inclination angle of approximately 45 degrees with respect to the illustrated rotation central axis, and a hemispherical ball lens. The light guided via the single mode fiber 342 is reflected on the mirror in a direction of approximately 90 degrees with respect to the traveling direction, and is emitted toward the vascular tissue indicated by an arrow 372a via the lens. Then, the light (arrow 372b) reflected from the vascular tissue is transmitted via the lens, and next time, the light is transmitted toward the MDU 102 (finally, to the operation control device 103) via the single mode fiber 342. During the scanning, the imaging core 250 is rotated. In this manner, similarly to the IVUS, data for reconstructing the vascular tomographic image can be acquired.

Hitherto, a structure of the distal portion of the hybrid type catheter has been described. In a case of the catheter dedicated to the IVUS, it is to be understood that the structure does not have the optical transceiver 352 and the fiber 274. In addition, in a case of the catheter dedicated to the OCT (OFDI), it is to be understood that the structure does not have the ultrasound transceiver 351 and the signal line cable 283.

Next, a process of determining a type of the catheter 101 connected to the MDU 102 according to the embodiment will be described. This determination process is performed by the signal processing unit 202.

As described above, the type of the catheter 101 can include three types such as a hybrid type, a type dedicated to the IVUS, and a type dedicated to the OCT. Among these, the hybrid type catheter is a type in which both the ultrasound transceiver 351 and the optical transceiver 352 are accommodated in the imaging core 250. The catheter dedicated to the IVUS is a type in which the ultrasound transceiver 351 is accommodated in the imaging core 250 without the optical transceiver 352 mounted thereon. Then, the catheter dedicated to the OCT is a type in which the optical transceiver 352 is accommodated in the imaging core 250 without the ultrasound transceiver 351 mounted thereon.

The configuration is adopted as described above. Accordingly, for example, assuming that the catheter 101 is connected to the MDU 102, an inspection process is performed as to whether or not the catheter 101 has the ultrasound transceiver 351 and whether or not the catheter 101 has the optical transceiver 352. In this manner, it is understood that the type of the connected catheter 101 can be determined based on the inspection result.

In a case where the catheter 101 has the optical transceiver 352, the light is emitted from the optical transceiver 352 toward an arrow 372a as illustrated in FIG. 3. The light has a property in which the light is reflected on a boundary surface of different materials. Therefore, some emitted light is reflected on the lens surface of the optical transceiver 352, the inner surface of the sheath 310, and the outer surface of the sheath 310, respectively. Accordingly, in the line data when the optical tomographic image is generated, concentric circles that are affected by the reflected light from these three places are generated at positions close to the rotation center. A concentric circle 403 in the vicinity of the rotation center 402 of the optical tomographic image illustrated in FIG. 4 just shows this image.

Figure 5:
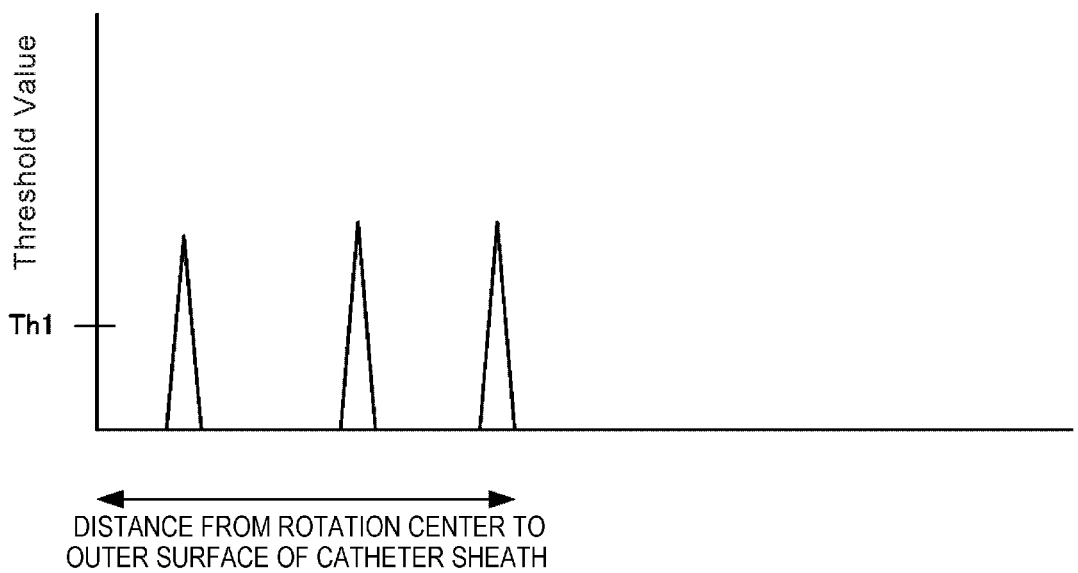
FIG. 5 is a view illustrating characteristics of line data for describing a principle of detecting an optical transceiver.

Therefore, the line data obtained by performing the fast Fourier transform (FFT) on the optical interference data is examined. If within a distance range from the rotation center position to the outer surface of the sheath 310, an inspection for detecting three peaks, which exceed a threshold value Th1 as illustrated in FIG. 5 is performed, it can be determined whether or not the optical transceiver 352 is present in the connected catheter 101. In a case where this condition is satisfied, it can be considered that the catheter having at least the optical transceiver 352 is connected to the MDU 102. In a case opposite thereto, it can be considered that the catheter having the optical transceiver 352 is not connected to the MDU 102.

In accordance with an exemplary embodiment, the reason is due to the structure of the distal portion of the catheter. Depending on the structure, the configuration is not limited to the three peaks. In addition, if the catheter is in a state of being accommodated inside a holder tube, the light is additionally reflected from the inner surface of the holder tube, and is reflected from the outer surface of the holder tube. That is, the catheter connection can be detected in accordance with a connection state of the catheter.

Furthermore, in the above-described configuration, based on a level of the signal reflected from the distal end of the catheter, it can be determined whether or not the catheter connection is connected. However, the connection portion between the MDU 102 and the catheter 101 can also perform similar detection. That is, for example, in a state where the catheter is not connected, the light is reflected from the end surface of the catheter 101 connected to the MDU 102. However, if the catheter 101 is connected, the reflected signal disappears. In accordance with an exemplary embodiment, the catheter connection can be determined by utilizing this fact.

Next, a method of inspecting the presence of the ultrasound transceiver 351 will be described.

Figure 6A:
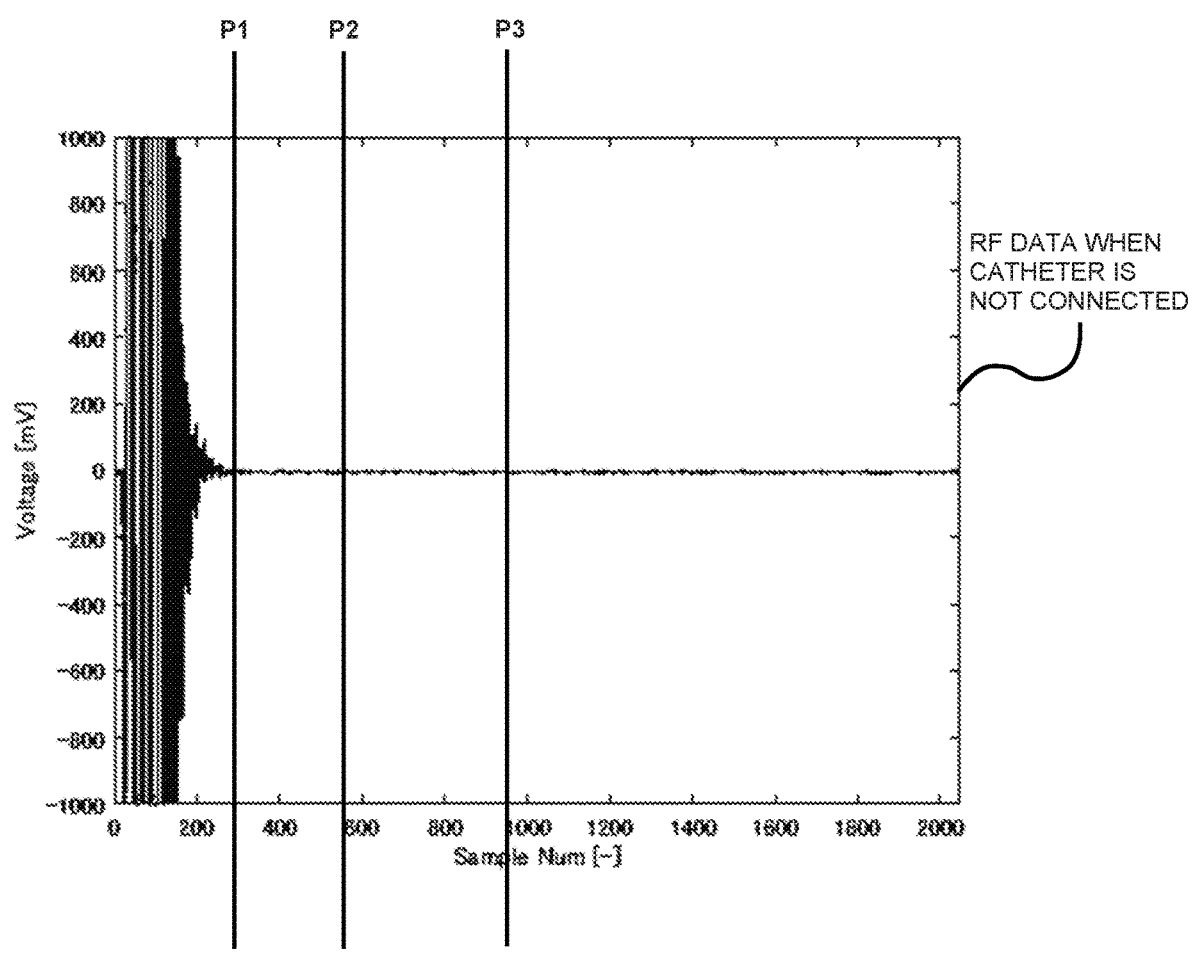
FIGS. 6A-6C are views illustrating characteristics of reflected wave data of an ultrasound wave for describing a principle of detecting an ultrasound transceiver.
Figure 6B:
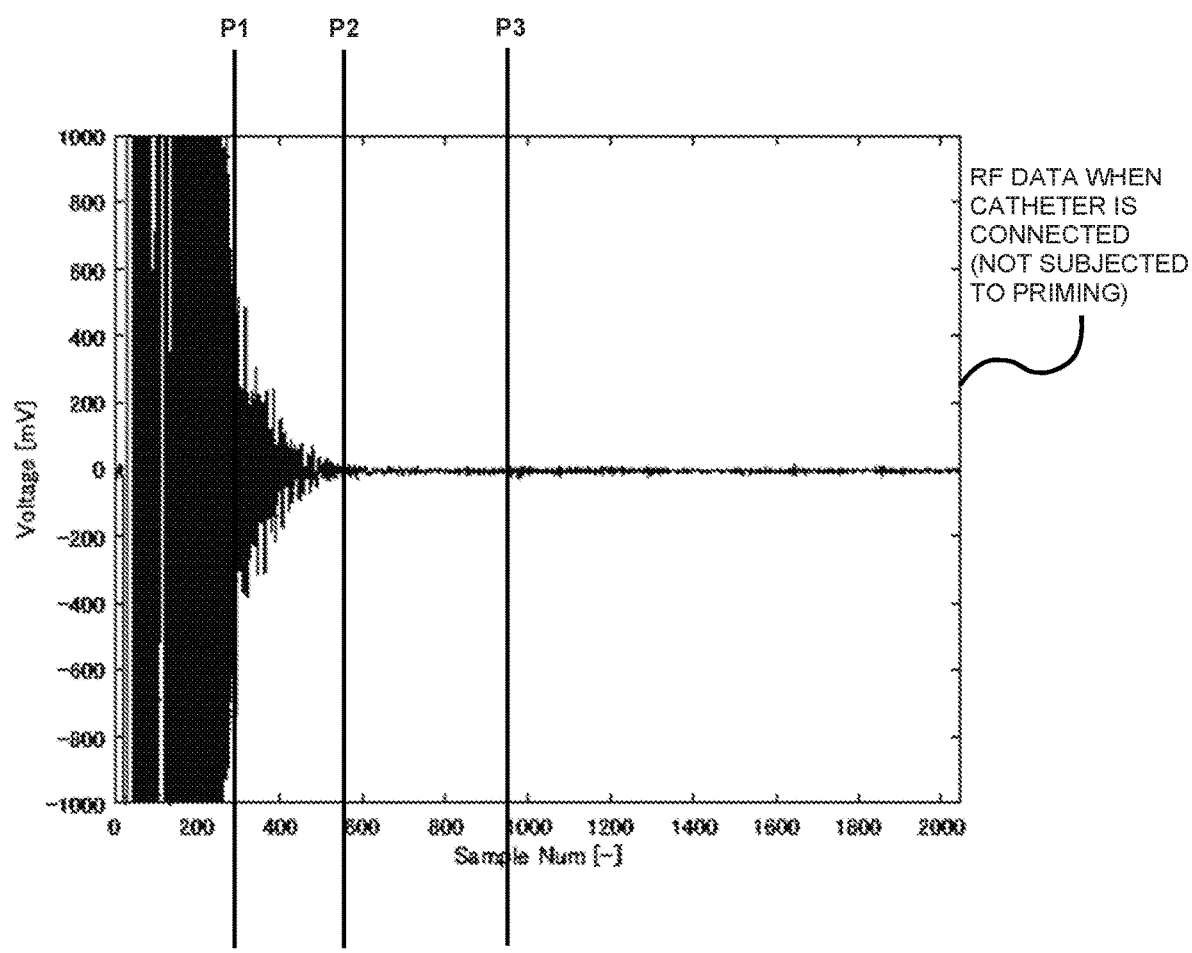

FIG. 6A illustrates reflected wave data (RF data) of the ultrasound wave obtained by the A/D converter 235, with respect to an output of the ultrasound drive signal in a case where the catheter is not connected to MDU 102 or in a case where the catheter dedicated to the OCT which does not have the ultrasound transceiver 351 is connected to the MDU 102. The illustrated horizontal axis represents a distance from the rotation center position (equivalent to the time required until the reflected wave is received), and the vertical axis represents intensity of the electric signal indicating the ultrasound wave.

In accordance with an exemplary embodiment, in a case where the catheter (the hybrid catheter, or the catheter dedicated to the IVUS) having the ultrasound transceiver 351 is used for a medical procedure, a priming operation (filling with a priming solution) is performed so as to remove the air inside the catheter. Thereafter, the catheter is connected to the MDU 102. However, even if the priming operation is not performed or even if the priming operation is performed, in a case where the air is mixed into the catheter 101 when being connected to the MDU 102, the reflected wave data as illustrated in the middle stage of the drawing is obtained. Even if the priming is not performed, or in a case where the air is present inside the catheter 101 even if the priming is performed, the reflected wave having intensity stronger than a certain level is detected even if the distance exceeds a point P1.

Figure 6C:
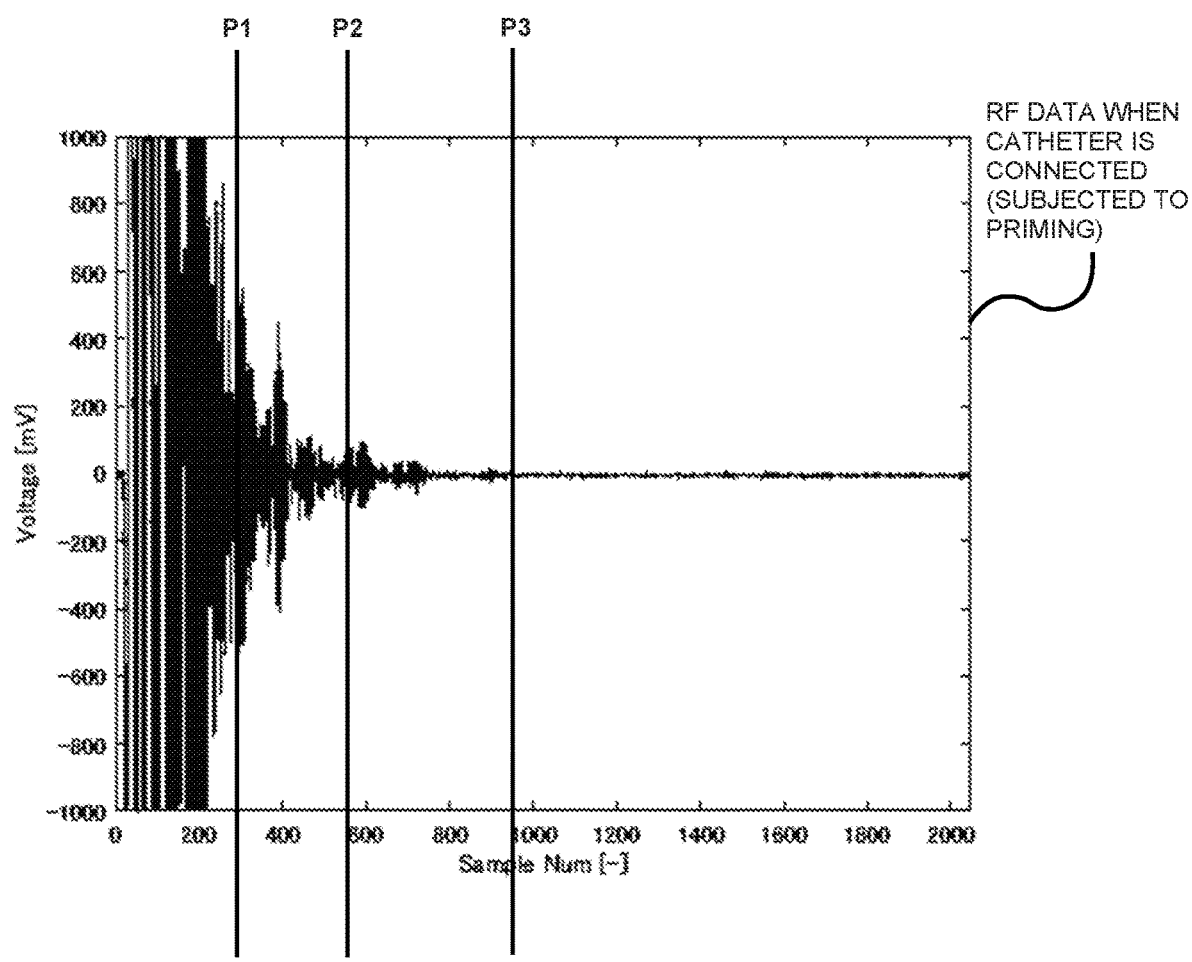

In addition, FIG. 6C illustrates the reflected wave data in a case where the catheter having the ultrasound transceiver 351, filled with the priming solution, and having no air bubble is connected to the MDU 102.

If the middle stage and the lower stage in the drawing are compared with each other, in a case where the priming is not performed or the air bubble is present, if the distance is farther than a point P2, the intensity of the reflected wave becomes almost zero. On the other hand, in a case where the priming is normally performed, the intensity of the reflected wave at a location farther than the point P2 does not become zero. When the distance exceeds a point P3, the intensity of the reflected wave becomes zero.

The configuration is adopted as described above. Accordingly, in the exemplary embodiment, the sum of absolute values of the reflected wave data within the points P1 to P3 in the reflected wave data can be calculated. In a case where the total value is equal to or smaller than a threshold value Th2, it can be determined that the catheter 101 having the ultrasound transceiver 351 is not connected to the MDU 102.

In accordance with an exemplary embodiment, in a case where the total value of the absolute values within the points P1 to P3 is greater than the threshold value Th2, it can be determined that the catheter 101 having at least the ultrasound transceiver 351 is connected to the MDU 102.

Furthermore, in this case, the sum of the absolute values of the reflected wave data within the points P2 to P3 can be calculated. In a case where the total value is greater than a threshold value Th3, it can be determined that the catheter 101 normally subjected to priming is connected to the MDU 102. In a case, for example, where the sum of the absolute values of the reflected wave data within the points P2 to P3 is equal to or smaller than the threshold value Th3, it can be determined that priming is not yet performed, or that the air is mixed into the catheter 101 for some reason after the priming operation (for example, an operation for connecting the catheter to the MDU 102). Although the line data depends on a system configuration, for example, when the line data of the ultrasound wave is configured to include 2,000 points (pixels), it can be desirable, for example, that P1 is $200^{th}$ point, P2 is $500^{th}$ point, and P3 is $1,000^{th}$ point.

In the above-described case, description is made so that the reflected wave data of the ultrasound wave is directly analyzed. However, the line data (image data) may be generated, and the inspection process may be performed by analyzing the line data. In a case of the line data, each pixel has only a positive value. Accordingly, it is unnecessary to obtain the absolute value.

Hitherto, the embodiment has been described. For example, the signal processing unit 201 may perform the process in accordance with a flowchart in FIG. 7. The process in the drawing is performed in a case where a user operates the operation panel 112 and instructs to determine the catheter 101. However, starting the process may be triggered even when power is turned on (in the latter case, the power is turned on after the catheter 101 is connected).

First, in Step S701, the signal processing unit 202 regards that the catheter 101 is connected to the MDU 102, and performs an inspection process of inspecting whether or not the optical transceiver 352 is present. Specifically, the signal processing unit 202 drives the wavelength swept light source 203 so as to transmit the light toward the MDU 102. Then, the optical interference data is acquired from the A/D converter 207, and is subjected to the FFT process so as to obtain the line data. Then, the signal processing unit 202 inspects whether or not three peaks exceeding the threshold value Th1 are present within a preset range from the end (corresponding to the rotation center position of the imaging core 250) in the line data.

In Step S702, the signal processing unit 202 determines whether or not the inspection result indicates the presence of the optical transceiver 352. In a case where the optical transceiver 352 is present, in Step S703, the signal processing unit 202 sets a flag F_OCT to "1". In a case of NO (a case where the optical transceiver 352 is not present), in Step S704, the signal processing unit 202 sets the flag F_OCT to "0".

Thereafter, in S705, the signal processing unit 202 regards that the catheter is connected to the MDU 102, and performs the inspection process of inspecting whether or not the ultrasound transceiver 351 is present. Specifically, a drive signal of the ultrasound wave is generated by the ultrasound transmitting/receiving control unit 232, and the reflected wave data of the ultrasound wave is acquired from the A/D converter 235. Then, as described previously, the sum of the absolute values of the reflected wave data within the points P1 to P3 is calculated, and is compared with the threshold value Th2. In a case where the total value is greater than the threshold value Th2, when the ultrasound transceiver 351 is present and the total value is equal to or smaller than the threshold value Th2, an inspection result indicating that the ultrasound transceiver 351 is not present is generated.

In S706, the signal processing unit 202 determines whether or not the inspection result indicates the presence of the ultrasound transceiver 351. In a case where the ultrasound transceiver 351 is present, in Step S707, the signal processing unit 202 sets a flag F_IVUS to "1". In a case of NO, in Step S708, the signal processing unit 202 sets the flag F_IVUS to "0". In a case where it is determined that the ultrasound transceiver 351 is not present, a process in S709 (to be described below) may be skipped, and flag F_PRM=0 may be set.

Next, in S709, the signal processing unit 202 inspects whether the catheter 101 connected to the MDU 102 can be normally used, that is priming of the catheter 101 has been performed. Specifically, the sum of the absolute values within the points P2 to P3 in the reflected wave data of the ultrasound wave is calculated, and is compared with the threshold value Th3. In a case where the sum of the absolute values exceeds the threshold value Th3, the inspection result indicating that the priming is normally performed is output. In a case where the sum is equal to or smaller (or less) than the threshold value Th3, it is considered that the priming is not performed, or a large amount of the air is mixed into the catheter 101. Accordingly, a result indicating abnormality can be output.

Then, in S710, the signal processing unit 202 determines whether or not the inspection result indicates that the priming is performed. In a case where it is determined that the priming is performed, in Step S711, the signal processing unit 202 sets the flag F_PRM to "1". In a case of NO, in Step S712, the signal processing unit 202 sets the flag F_PRM to "0".

Thereafter, in Step S713, the signal processing unit 202 determines a type of the catheter connected to the MDU 102, based on each flag confirmed so far.

Specifically, the type is determined as follows.

In a case of the flag F_IVUS=1 and the flag F_OCT=1, it can be determined that the connected catheter 101 is the hybrid type catheter.

In a case of the flag F_IVUS=0 and the flag F_OCT=1, it can be determined that the connected catheter 101 is the catheter dedicated to the OCT.

In a case of the flag F_IVUS=1 and the flag F_OCT=0, it can be determined that the connected catheter 101 is the catheter dedicated to the IVUS.

In a case of the flag F_IVUS=0 and the flag F_OCT=0, it can be determined that the catheter is not connected to the MDU 102 or determined as error.

Furthermore, in a case of the flag F_PRM=1, the signal processing unit 202 determines that the priming is performed. In a case of the flag F_PRM=0, the signal processing unit 202 determines as abnormality or error since the priming is not normally performed.

Then, in S714, based on the above-described determination result, the signal processing unit 202 causes a monitor 113 to display the type of the determined catheter 101, a state where the priming is performed, abnormality, or the presence or absence of the error.

In a case of the catheter having the ultrasound transceiver 351 (either the hybrid catheter or the catheter dedicated to the IVUS), a special warning may be issued in order to indicate that the medical procedure is not available if the priming is not performed.

In addition, in a case where there is no catheter 101 connected to the MDU 102, in addition to a case where the catheter 101 is not actually connected to the MDU 102, there is a possibility that communication with the MDU 102 may be in disorder. Accordingly, an error message confirming the connection relationship may be displayed.

Hitherto, the embodiment according to the present disclosure has been described. As can be understood from the above description, the process according to the embodiment is performed. In this manner, it is possible to determine the type of the catheter 101 without needing to provide a special mechanism (a physical switch or a sensor) for determining the type of the catheter 101.

In addition, as described in the embodiment, most of the characteristics can be realized by performing the process of the signal processing unit 202. The signal processing unit 202 is configured to include a CPU, and causes the CPU to execute a program. Therefore, it is obvious that the scope of the present disclosure also includes the program.

The present invention is not limited to the above-described embodiment, and various modifications and alterations can be made without departing from the spirit and scope of the present invention. Accordingly, in order to officially announce the scope of the present disclosure, claims are appended as follows.

The detailed description above describes an imaging apparatus for diagnosis using a catheter, and an operation method and a program thereof. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis comprising:
 a motor drive unit configured to be connected to a catheter and configured to move and rotate an imaging core accommodated in the catheter along a longitudinal direction of the catheter, the imaging core configured to generate a vascular optical coherence tomographic image and/or an ultrasound tomographic image of a subject, based on a signal output from the catheter; and
 a processor configured to:
  apply an ultrasound drive signal to an ultrasound transceiver accommodated in a distal portion of the imaging core, and acquire an electric signal indicating a reflected wave, when the catheter is connected to the motor drive unit;
  supply light to an optical transceiver accommodated in the distal portion of the imaging core, and acquire an electric signal indicating interference light, when the catheter is connected to the motor drive unit;
  determine a presence or an absence of the ultrasound transceiver, based on intensity distribution of the acquired electric signal of the reflected wave and/or generate line image data in a radial direction, regarding a position of the imaging core as an origin, based on the acquired electric signal of the interference light, and determine a presence or an absence of the optical transceiver, based on pixel data distribution within a predetermined range from a position of the origin; and
  determine whether the catheter connected to the motor drive unit is any one of an ultrasound tomographic imaging catheter, a vascular optical coherence tomographic imaging catheter, or an ultrasound and vascular optical coherence tomographic imaging catheter, based on a result of the determination of the presence or the absence of the ultrasound transceiver and/or the determination of the presence or the absence of the optical transceiver.

2. The imaging apparatus for diagnosis according to claim 1,
 wherein the result obtained indicate the presence of the ultrasound transceiver and the optical transceiver, the processor is configured to determine that the catheter is connected to the motor drive unit is the ultrasound and vascular optical coherence tomographic imaging catheter;
 wherein the result obtained indicate the presence of the ultrasound transceiver and the absence of the optical transceiver, the processor is configured to determine that the catheter connected to the motor drive unit is the ultrasound tomographic imaging catheter;
 wherein the result obtained indicate the absence of the ultrasound transceiver and the presence of the optical transceiver, the processor is configured to determine that the catheter connected to the motor drive unit is the vascular optical coherence tomographic imaging catheter; and
 wherein result obtained indicate the absence of the ultrasound transceiver and the absence of the optical transceiver, the processor is configured to determine that the catheter is not connected to the motor drive unit.

3. The imaging apparatus for diagnosis according to claim 1, wherein the processor is further configured to:
 determine whether or not the connected catheter is subjected to priming, or whether or not the connected catheter is not subjected to priming, based on the intensity distribution of the acquired electric signal of the reflected wave.

4. The imaging apparatus for diagnosis according to claim 1, further comprising:
 a display unit configured to display the determination of whether the catheter connected to the motor drive unit is any one of the ultrasound tomographic imaging catheter, the vascular optical coherence tomographic imaging catheter, or the ultrasound and vascular optical coherence tomographic imaging catheter.

5. An operation method of an imaging apparatus for diagnosis which has a motor drive unit configured to be connected to a catheter and for moving and rotating an imaging core accommodated in the catheter along a longitudinal direction of the catheter, and which is configured to generate a vascular optical coherence tomographic image and/or an ultrasound tomographic image of a subject, based on a signal output from the catheter, the method comprising:
 connecting the catheter to the motor drive unit;
 applying an ultrasound drive signal to an ultrasound transceiver accommodated in a distal portion of the imaging core, and acquiring an electric signal indicating a reflected wave, when the catheter is connected to the motor drive unit;
 supplying light to an optical transceiver accommodated in the distal portion of the imaging core, and acquiring an electric signal indicating interference light, when the catheter is connected to the motor drive unit;
 determining a presence or an absence of the ultrasound transceiver, based on intensity distribution of the acquired electric signal of the reflected wave and/or generating line image data in a radial direction, regarding a position of the imaging core as an origin, based on the acquired electric signal of the interference light, and determining a presence or an absence of the optical transceiver, based on pixel data distribution within a predetermined range from a position of the origin; and
 determining whether the catheter connected to the motor drive unit is any one of an ultrasound tomographic imaging catheter a vascular optical coherence tomographic imaging catheter, or an ultrasound and vascular optical coherence tomographic imaging catheter, based on the determination of the presence or the absence of the ultrasound transceiver and/or the determination of the presence or the absence of the optical transceiver.

6. The method according to claim 5, further comprising:
 determining, that the catheter connected to the motor drive unit is the ultrasound and vascular optical coherence tomographic imaging catheter when the presence of the ultrasound transceiver and the optical transceiver is determined,
 determining that the catheter connected to the motor drive unit is the ultrasound tomographic imaging catheter when the presence of the ultrasound transceiver and the absence of the optical transceiver is determined;
 determining that the catheter connected to the motor drive unit is the vascular optical coherence tomographic imaging catheter when the absence of the ultrasound transceiver and the presence of the optical transceiver is determined; and
 determining that the catheter is not connected to the motor drive unit when the absence of the ultrasound transceiver and the absence of the optical transceiver is determined.

7. The method according to claim 5, further comprising:
determining whether or not the connected catheter is subjected to priming, or whether or not the connected catheter is not subjected to priming, based on the intensity distribution of the electric signal of the reflected wave.

8. The method according to claim 5, further comprising: displaying the determination of whether the catheter connected to the motor drive unit is any one of the ultrasound tomographic imaging catheter, the vascular optical coherence tomographic imaging catheter or the ultrasound and vascular optical coherence tomographic imaging catheter.

9. A non-transitory computer readable medium, the non-transitory computer readable medium having instructions operable to cause one or more processors to execute each process described in claim 5.

10. A method for determining a type of catheter connected to a motor drive unit of an imaging apparatus for diagnosis, wherein the motor drive unit is configured to be connected to a catheter and to move and rotate an imaging core accommodated in the catheter along a longitudinal direction of the catheter, and configured to generate a vascular optical coherence tomographic image and/or an ultrasound tomographic image of a subject, based on a signal output from the catheter, the method comprising:
connecting the catheter to the motor drive unit;
applying an ultrasound drive signal to an ultrasound transceiver accommodated in a distal portion of the imaging core, and acquiring an electric signal indicating a reflected wave, when the catheter is connected to the motor drive unit;
supplying light to an optical transceiver accommodated in the distal portion of the imaging core, and acquiring an electric signal indicating interference light, when the catheter is connected to the motor drive unit;
determining a presence or an absence of the ultrasound transceiver, based on intensity distribution of the acquired electric signal of the reflected wave and/or generating line image data in a radial direction, regarding a position of the imaging core as an origin, based on the acquired electric signal of the interference light, and determining a presence or an absence of the optical transceiver, based on a pixel data distribution within a predetermined range from a position of the origin; and
determining whether the catheter connected to the motor drive unit is any one of an ultrasound tomographic imaging catheter, a vascular optical coherence tomographic imaging catheter, or an ultrasound and vascular optical coherence tomographic imaging catheter, based on the intensity distribution of the acquired electric signal of the reflected wave and/or the pixel data distribution within the predetermined range from the position of the origin.

11. The method according to claim 10, further comprising:
determining that the catheter connected to the motor drive unit is the ultrasound and vascular optical coherence tomographic imaging catheter when the presence of the ultrasound transceiver and the presence of the optical transceiver is determined.

12. The method according to claim 10, further comprising:
determining that the catheter connected to the motor drive unit is the ultrasound tomographic imaging catheter when the presence of the ultrasound transceiver and the absence of the optical transceiver is determined.

13. The method according to claim 10, further comprising:
determining that the catheter connected to the motor drive unit is the vascular optical coherence tomographic imaging catheter when the absence of the ultrasound transceiver and the presence of the optical transceiver is determined.

14. The method according to claim 10, further comprising:
determining that the catheter is not connected to the motor drive unit when the absence of the ultrasound transceiver and the absence of the optical transceiver is determined.

15. The method according to claim 10, further comprising:
determining whether or not the connected catheter is subjected to priming or whether or not the connected catheter is not subjected to priming, based on the intensity distribution of the acquired electric signal of the reflected wave.

16. The method according to claim 10, wherein the presence or the absence of the optical transceiver, based on the pixel data distribution within the predetermined range from the position of the origin further comprises:
driving a wavelength swept light source so as to transmit the light toward the motor drive unit;
acquiring optical interference data from an A/D converter;
subjecting the optical interference data to a fast Fourier transform (FFT) process to obtain line data; and
determining whether or not peaks associated with optical interference data exceeding a first threshold value are present in the line data within the predetermined range.

17. The method according to claim 10, wherein the determining of the presence of the ultrasound transceiver, based on the intensity distribution of the acquired electric signal of the reflected wave, further comprises:
calculating a sum of absolute values of the acquired electric signal indicating the reflected wave within a plurality of data points;
determining that the catheter having the ultrasound transceiver is not connected to the motor drive unit when a total value of the sum of the absolute values of the reflected wave data within the plurality of data points is equal to or smaller than a first threshold value; and
determining that the catheter having the ultrasound transceiver is connected to the motor drive unit when where the total value of the absolute values within the plurality of data points is greater than the first threshold value.

18. The method according to claim 17, further comprising:
determining that the catheter connected to the motor drive unit is subjected to priming, when a sum of the absolute values of the reflected wave data within at least two data points of the plurality of data points is greater than a second threshold value; and
determined that priming is not yet performed, or that air is mixed into the catheter after the priming operation when the sum of the absolute values of the reflected wave data within the at least two data point of the plurality of data points is equal to or less than a third threshold value.

19. The method according to claim 10, further comprising: displaying the determination of whether the catheter connected to the motor drive unit is any one of the ultrasound tomographic imaging catheter, the vascular optical coherence tomographic imaging catheter, or the ultrasound and vascular optical coherence tomographic imaging catheter.

20. A non-transitory computer readable medium, the non-transitory computer readable medium having instructions operable to cause one or more processors to execute each process described in claim 10.

* * * * *